United States Patent [19]

Fenton

[11] Patent Number: 4,578,375

[45] Date of Patent: Mar. 25, 1986

[54] LANTHANUM HYDROXIDE AND A RHODIUM OR RUTHENIUM MOIETY CATALYST FOR HOMOLOGATION OF ALCOHOLS

[75] Inventor: Donald M. Fenton, Anaheim, Calif.

[73] Assignee: Union Oil Company of California, Los Angeles, Calif.

[21] Appl. No.: 740,235

[22] Filed: May 31, 1985

Related U.S. Application Data

[62] Division of Ser. No. 643,835, Aug. 24, 1984, Pat. No. 4,540,836.

[51] Int. Cl.$^4$ .................. B01J 27/10; B01J 23/46; C07C 29/00; C07C 31/08
[52] U.S. Cl. .................. 502/230; 502/84; 502/181; 502/303; 568/902
[58] Field of Search .............. 502/230, 181, 303, 525; 423/21.1, 263, 213.5

[56] References Cited

U.S. PATENT DOCUMENTS

| | | | |
|---|---|---|---|
| 3,717,670 | 2/1973 | Schultz | 502/150 |
| 4,001,143 | 1/1977 | McCann | 423/213.5 |
| 4,126,752 | 11/1978 | Novotny | 568/902 |
| 4,134,852 | 1/1979 | Volin | 502/525 |
| 4,140,655 | 2/1979 | Chabot et al. | 502/525 |
| 4,148,715 | 4/1979 | Anjus | 502/230 |
| 4,312,955 | 1/1982 | Bartley | 568/716 |
| 4,401,557 | 8/1983 | Juguim et al. | 502/230 |

FOREIGN PATENT DOCUMENTS 254819 7/1926 United Kingdom .............. 568/902

*Primary Examiner*—P. E. Konopka
*Attorney, Agent, or Firm*—Gregory F. Wirzbicki; Dean Sandford; Robert J. Baran

[57] ABSTRACT

This invention provides a novel heterogeneous catalyst system adapted for alkanol homologation, which comprises lanthanum hydroxide and a rhodium or ruthenium moiety, e.g. $RhCl_3$ or $RuCl_3$.

8 Claims, No Drawings

LANTHANUM HYDROXIDE AND A RHODIUM OR RUTHENIUM MOIETY CATALYST FOR HOMOLOGATION OF ALCOHOLS

This application is a division of application Ser. No. 643,835, filed Aug. 24, 1984, now U.S. Pat. No. 4,540,836.

BACKGROUND OF THE INVENTION

1. Field of the Invention

This invention relates to a process for the homologation of methanol, or other lower alkanols, e.g. monohydroxy-$C_1$ to $C_3$ alkanols, into higher alkanols, i.e. alkanols having more carbon atoms than the starting alkanol, e.g. $C_2$ to $C_4$ alkanols, by contacting said lower alkanol with carbon monoxide, in the presence of a catalyst comprising a lanthanum moiety.

2. Description of the Art

There are various processes for preparing methanol, from carbon monoxide and hydrogen. For example, Magoon et al. in U.S. Pat. No. 3,758,417 teaches the preparation of methanol by reacting carbon monoxide and hydrogen, in the presence of a catalyst, comprising didymium in combination with copper and zinc. Bartley, in U.S. Pat. No. 4,312,955, discloses a lanthanum rhodate, having a perovskite structure, as a catalyst, for the same reaction.

Various references disclose the homologation of methanol with carbon monoxide and hydrogen in the presence of cobalt or rhodium catalysts. See patents to Taylor, i.e. U.S. Pat. No. 4,111,837 and 4,150,246, which disclose the homologation of alkanols in the presence of a catalyst system consisting essentially of cobalt carbonyl and rhenium metal. Slinkard et al., in U.S. Pat. No. 4,168,391, disclose an improved process for homologating methanol with carbon monoxide and hydrogen, in the liquid phase, and in the presence of a cobalt carbonyl catalyst. Bartish, in U.S. Pat. No. 4,171,461, also teaches the conversion of methanol to ethanol by reaction with hydrogen and carbon monoxide in the presence of a cobalt catalyst. In this invention, the improvement resides in the selection of the particular catalyst; however, it is clear that the catalyst must contain cobalt. Forrester, in U.S. Pat. No. 4,190,729, also teaches that a cobalt carbonyl catalyst is useful in the carbonylation of methanol to ethanol, acetaldehyde and methyl acetate. In this patent the improvement resides in using a tertiary phosphine oxide as a stabilizer for the cobalt carbonyl catalyst. Hargis et al., in U.S. Pat. Nos. 4,309,314 and 4,361,499, disclose reacting methanol with hydrogen and carbon monoxide, in the presence of catalyst comprising rhodium and iron, to provide ethanol and methyl acetate. This catalyst may also comprise a minor amount of an alkaline metal or a heterocyclic amine promoter to enhance the formation of a substantial portion of ethanol and methyl acetate. A tertiary amine is used as a promoter in Feder et al., U.S. Pat. No. 4,386,009, wherein the conversion of methanol to ethanol, by reaction with carbon monoxide and hydrogen, is disclosed. Finally, Kummer et al., U.S. Pat. No. 4,454,358, teach that ethanol may be produced, continuously, by the carbonylation of methanol with carbon monoxide and hydrogen, in the presence of a Group VIII carbonyl catalyst and a halogen compound. In the processes disclosed in the above references, extensive quantities of hydrogen are undesirably consumed.

In one reference, Schultz, U.S. Pat. No. 3,717,670, it is taught that alcohols may be reacted with carbon monoxide, in the presence of a catalyst comprising a rhodium component, in combination with a metal compound selected from the IB, IIB, IVB, VB, VIB and VIII, lanthanide and actinide groups of the Periodic Table of the Elements, to provide organic acids and organic esters. This reference indicates that a halide promoter is a necessary component of the catalyst. The process disclosed in reference is carried out in the absence of hydrogen; however the reaction product is acetic acid, not a higher alcohol.

Accordingly, it is an object of this invention to provide an improved process for homologation of alkanols with carbon monoxide.

It is another object of this invention to provide a novel heterogenous catalyst adapted for conversion of methanol to ethanol and higher alkanols.

It is a further object of this invention to provide a process for preparing an improved catalyst system for the liquid phase homologation of alkanols.

Other objects and advantages of this invention shall become apparent from the following description and exemplary data.

SUMMARY OF THE INVENTION

The present invention provides a homologation process for producing ethanol or higher alkanols which comprises reacting methanol or a higher alkanol with carbon monoxide in the liquid phase and in the presence of a catalyst comprising a lanthanum moeity, preferably a methanol-insoluble lanthanum moeity, e.g. lanthanum hydroxide. This process is carried out in the absence of added hydrogen and at a pH of at least 7.0. Preferably, the catalyst further comprises a rhodium or ruthenium moiety, e.g. a methanol-insoluble ruthenium or rhodium compound or salt, such as $RhCl_3$ or $RuCl_3$. The above process may be carried out at a temperature of from 100° C. to 450° C. and at a pressure of from 1 atmosphere to 500 atmospheres.

The process of this invention has general applicability of the homologation of alkanols, substituted alkanols, alkane polyols, and the like. While preferably the alkanols are lower monohydroxy alkanols, preferably containing one to three carbon atoms, e.g. methanol, the homologation of alkanols having up to 12 carbon atoms (e.g. decanol), polyhydroxy alkanols (e.g. ethylene glycol), and substituted alkanols (e.g., benzyl alcohol) is readily accomplished by the present invention.

DETAILED DESCRIPTION OF THE INVENTION

The instant invention provides a process for converting an alkanol reactant into alkanols having at least one or more carbon atoms than said alkanol reactant which comprises contacting a solution, having a pH of greater than 7.0 and comprising said alkanol reactant, with carbon monoxide, in the presence of a catalyst comprising lanthanum, and in the absence of added hydrogen.

The alkanol being reacted provides the liquid phase reaction medium for the process of this invention. If desired, an alkanol-miscible diluent such as dioxane, tetrahydrofuran, water and the like may be included to moderate the rate and the exothermic heat of the reaction.

Illustrative of a typical process of this invention, methanol is charged to an autoclave reactor, and then a catalyst system of a lanthanum moiety, preferably a methanol-insoluble lanthanum moiety, e.g. lanthanum hydroxide, is introduced. More preferably, a methanol-insoluble rhodium or ruthenium salt or compound is also included, along with the lanthanum moiety, as is more fully described hereinbelow. The reactor is pressurized with a gaseous mixture comprising carbon monoxide. Mixtures of carbon monoxide and carbon dioxide or water, and the like, may also be employed. Whether introduced originally, or produced in-situ during processing, a carbon monoxide reactant is required. The relative molar quantities of carbon monoxide and the alkanol reactant can vary in the range between about 30:1 and 1:300, and preferably in the range between about 10:1 and 1:10. An inert diluent gas such as nitrogen or helium may be included if desired. The homologation reaction requires a relatively high pressure for optimum yield of homologation product. The pressure is preferably maintained in the range between about 1,000 and 15,000 p.s.i.g., and more preferably in the range between about 2,000 and 10,000 p.s.i.g.

The homologation reaction is preferably conducted at a temperature in the range between about 100° C. and 450° C. The preferred temperature range for homologation of methanol to ethanol is between about 350° C. and 450° C.

The reaction period which is optimum for a particular alkanol will vary depending on the pressure and temperature and CO:alkanol molar ratio. Normally, the reaction period can vary in the range between about 2 minutes and 10 hours. In a typical operation the optimum reaction period will be in the range between about 2 and 6 hours. A suitable reaction period for methanol homologation is about 6 hours at about 390° C. and 2,000 to 4,000 p.s.i.g.

The invention process can be conducted either continuously or batchwise. In a continuous process, a high pressure separator can be employed to remove the reaction products from the reactor effluent stream, and the unreacted carbon monoxide can be recycled.

The product mixture recovered from methanol homologation consists of ethanol, dimethyl ether, methyl acetate, ethyl acetate and methyl propionate. When a rhodium moiety is included, the product mixture may further include isobutanol and 2-methyl-1-butanol. If desired, methyl acetate can be recycled to produce ethanol under the conditions of the process of this invention. Water in some form is necessary as a source of hydrogen. (One of the advantages of this invention is utilizing water, as an inexpensive source of hydrogen.) Water can be included in the liquid phase reaction medium or obtained from the hydroxide added, e.g. lanthanum hydroxide or the basic materials indicated below, or even spuriously from methanol dehydration to methyl ether.

The catalyst utilized in the process of the present invention comprises a lanthanum moiety. It is preferred that said lanthanum moiety be insoluble in the methanol or alkanol reactant solution, i.e., it is preferable to operate in a heterogenous catalyst mode. Therefore methanol-insoluble salts of lanthanum such as the halides, oxides or the hydroxide are preferred. The lanthanum salts having basic characteristics, e.g. lanthanum hydroxide, are even more preferred since the reaction is carried out under basic conditions, i.e. at a pH greater than 7.0. and these basic lanthanum salts provide the necessary basicity in the reactant solution. The other lanthanum salts mentioned above require the addition of a basic material, such as the oxides and hydroxides of Group I and II of the Periodic Table of the elements, e.g. NaOH, KOH, Ca(OH$_2$), MgO etc. to the reactant solution to provide the necessary basicity. Finally, lanthanum hydroxide is the most preferred source of lanthanum for providing water as a source of hydrogen for the process of this invention.

The surface area of the lanthanum moiety is maximized to increase the rate of reaction. Preferably the reaction is carried out in the presence of a rhodium or ruthenium moiety, in addition to the above lanthanum moiety. The rhodium and ruthenium moiety may be provided by including a rhodium or ruthenium compound or salt in the methanol reactant solution. Like the lanthanum moiety, it is preferred that the rhodium or ruthenium be in the form of a methanol-insoluble salt or compound for operation in the heterogenous mode. Suitable methanol-insoluble ruthenium and rhodium sources include rhodium and ruthenium oxides which can also be generated in-situ from rhodium or ruthenium halides. When operating in the heterogeneous mode, it is of course preferable to provide the ruthenium and rhodium in a high surface area form. Physical methods suitable for preparing high surface area lanthanum salts or compounds, such as grinding, etc., may also be used to provide high surface area rhodium or ruthenium salts or compounds.

The rhodium or ruthenium moiety may also be provided in physical or chemical combination with the lanthanum moiety, e.g. by supporting the rhodium or ruthenium moiety on the lanthanum moiety. Alternatively, both the lanthanum and rhodium or ruthenium moieties can be supported on carrier materials known in the art, e.g. alumina and other refractory inorganic oxides, clays, high surface area carbon, etc. Utilizing a mixed oxide or rhodium or ruthenium and lanthanum such as lanthanum rhodate, or lanthanum ruthenate as the catalyst, is a suitable method for providing lanthanum and rhodium or ruthenium in combination. In addition, either lanthanum metal and rhodium or ruthenium metal may be used to provide the catalyst for the process of the present invention, since at the reaction conditions indicated above, such metals react with methanol (or other alkanols) to provide the oxide.

The catalyst may be formed into granules or pellets and charged to a fixed bed as an integrated unit in a continuous alkanol homologation process.

In the preferred catalyst system of the present invention, the atomic ratio of lanthanum to rhodium or ruthenium can vary in the range between about 0.001 and 50 to 1, and preferably in the range between about 0.001 and 1 to 1.

In the homologation process of this invention, as conducted batch-wise, the quantity of lanthanum, on an atomic weight basis, can vary between about 0.001 and 20 weight percent, based on the alkanol present.

The invention is further illustrated by the following examples which are illustrative of specific mode of practicing the invention and are not intended as limiting the scope of the appended claims.

EXAMPLE 1

To 25 ml methanol and 15 g lanthanum hydroxide in a glass tube contained in a steel bomb is added carbon monoxide to 600 p.s.i.g. The mixture is heated to 390° C. and held thereat for 6 hours. The liquid resulting (10.4 g) is analyzed by GC and found to contain 0.7% methyl ether, 59.7% methanol, 2.9% ethanol, 24.5% water, 7.0% g methyl acetate, 1.9% ethyl acetate and 1.5% methyl propionate.

EXAMPLE 2

The above example is repeated except that 0.2 rhodium trichloride.3H$_2$O is also used. There results a liquid which contains 5.6% CO$_2$, 21.9% methanol, 2.3% ethanol, 3% propanol, 5% isobutyl alcohol, 0.8 2-methyl-1-butanol, 1% another alcohol and 58% water.

While particular embodiments of the invention have been described, it will be understood, of course, that the invention is not limited thereto since many obvious modifications can be made and it is intended to include within this invention any such modifications as will fall within the scope of the appended claims.

I claim:

1. A catalyst for the homologation of alcohols consisting essentially of a rhodium moiety supported on lanthanum hydroxide wherein the atomic ratio of lanthanum to rhodium is in the range between about 0.001 and 50 to 1.

2. The catalyst of claim 1 wherein said rhodium moiety is RhCl$_3$.

3. A method of preparing a catalyst for the homologation of alcohols which comprises combining, in a liquid phase reaction medium comprising alcohol, lanthanum hydroxide and a rhodium salt or compound, insoluble in said reaction medium.

4. The method of claim 3 wherein said rhodium salt or compound is RhCl$_3$.

5. A catalyst for the homologation of alcohols consisting essentially of a ruthenium moiety supported on lanthanum hydroxide wherein the atomic ratio of lanthanum to ruthenium is in the range between about 0.001 and 50 to 1.

6. The catalyst of claim 5 wherein said ruthenium moiety is RuCl$_3$.

7. A method of preparing a catalyst for the homologation of alcohols which comprises combining, in a liquid phase reaction medium comprising alcohol, lanthanum hydroxide and a ruthenium salt or compound, insoluble in said reaction medium.

8. The method of claim 7 wherein said ruthenium salt or compound is RuCl$_3$.

* * * * *